US009953735B2

(12) United States Patent
Bar-David et al.

(10) Patent No.: US 9,953,735 B2
(45) Date of Patent: Apr. 24, 2018

(54) X-RAY REFLECTIVE LENS ARRANGEMENT

(71) Applicant: CONVERGENT R.N.R LTD, Tirat Carmel (IL)

(72) Inventors: Aharon Bar-David, Nesher (IL); Zeev Burshtein, Nes-Ziona (IL); Zeev Harel, Kfar Saba (IL)

(73) Assignee: CONVERGENT R.N.R LTD, Tirat Carmel (IL)

( * ) Notice: Subject to any disclaimer, the term of this patent is extended or adjusted under 35 U.S.C. 154(b) by 488 days.

(21) Appl. No.: 14/430,683

(22) PCT Filed: Sep. 1, 2013

(86) PCT No.: PCT/IL2013/050739
§ 371 (c)(1),
(2) Date: Mar. 24, 2015

(87) PCT Pub. No.: WO2014/045273
PCT Pub. Date: Mar. 27, 2014

(65) Prior Publication Data
US 2015/0248942 A1    Sep. 3, 2015

Related U.S. Application Data

(60) Provisional application No. 61/704,588, filed on Sep. 24, 2012.

(51) Int. Cl.
*G21K 1/00*    (2006.01)
*G21K 1/06*    (2006.01)
(Continued)

(52) U.S. Cl.
CPC .......... *G21K 1/062* (2013.01); *A61N 5/1042* (2013.01); *A61N 5/1084* (2013.01);
(Continued)

(58) Field of Classification Search
CPC .......... A61N 5/1084; A61N 2005/1095; A61N 5/1042; A61N 2005/1061; A61N 5/1049;
(Continued)

(56) References Cited

U.S. PATENT DOCUMENTS 5,071,207 A    12/1991   Ceglio et al.
5,339,346 A    8/1994    White
(Continued)

FOREIGN PATENT DOCUMENTS

WO    WO/2001/046961 A1    6/2001
WO    WO/2014/045273 A1    3/2014

OTHER PUBLICATIONS

International Search Report for PCT/IL2013/050739, dated Dec. 31, 2011.
(Continued)

*Primary Examiner* — Irakli Kiknadze

(57) ABSTRACT

An X-ray lens arrangement for forming a radiation pattern as a focal track is disclosed. The pattern comprises at least one 3-dimensional focal track of radiation. The aforesaid lens arrangement has a main axis passing through intensity weighted centroids of the X-ray source and the pattern. The lens arrangement includes at least one reflecting surface of continuously varying Rowland arcs. Each point belonging to the focal track is linked to each elemental point composing an emitting surface of said source by a corresponding Rowland arc.

8 Claims, 17 Drawing Sheets

(51) Int. Cl.
*A61N 5/10* (2006.01)
*G21K 5/04* (2006.01)

(52) U.S. Cl.
CPC ............... *A61N 2005/1091* (2013.01); *A61N 2005/1095* (2013.01); *G21K 5/04* (2013.01); *G21K 2201/064* (2013.01)

(58) Field of Classification Search
CPC ............... A61N 5/1065; A61N 5/1077; A61N 2005/1098; A61N 5/10; A61N 2005/1091; G21K 2201/064; G21K 5/04; G21K 1/04; G21K 1/06; G21K 1/065; G21K 1/067; G21K 1/062; G21K 2201/067; G21K 2201/061; G21K 2207/005; G21K 1/00; G21K 1/02; G21K 2201/06; G21K 1/10; G21K 2201/062; G21K 1/025; G21K 1/046; G21K 1/08; F16K 31/08; G02B 17/00; H01L 2924/0002; H01L 2924/00; B82Y 10/00; G06K 19/07745; Y10T 156/10; Y10T 156/1075

USPC .................... 378/60, 71, 73, 84, 145
See application file for complete search history.

(56) References Cited

U.S. PATENT DOCUMENTS

| | | |
|---|---|---|
| 5,982,562 A | 11/1999 | Rode |
| 6,014,423 A | 1/2000 | Gutman et al. |
| 6,389,100 B1 | 5/2002 | Verman et al. |
| 7,068,754 B2 | 6/2006 | Goebel et al. |
| 2005/0218353 A1 | 10/2005 | Liang |
| 2010/0085272 A1 | 4/2010 | Legay et al. |
| 2011/0280530 A1 | 11/2011 | Verman et al. |

OTHER PUBLICATIONS

Written Opinion of the International Search Authority for PCT/IL2013/050739, dated Dec. 31, 2013.
International Preliminary Report on Patentability (Chapter I), dated Mar. 24, 2015.

X-RAY REFLECTIVE LENS ARRANGEMENT

FIELD OF THE INVENTION

The present invention relates to an X-ray lens and, more specifically, to an X-ray lens arrangement configured for focusing a radiation from an X-ray source into a curved radiation pattern in a volume of radiotherapy treatment.

BACKGROUND OF THE INVENTION

According to conventional radiation therapy, a radiation beam is directed towards a tumor located within a patient's body. The radiation beam delivers a predetermined dose of therapeutic radiation to the tumor according to an established therapy plan. The delivered radiation kills tumor cells by causing ionizations within the cells. In this regard, radiation therapy systems are designed to maximize radiation delivered to the tumor while minimizing radiation delivered to healthy tissue.

U.S. Pat. No. 6,389,100 discloses a modular X-ray lens system for use in directing X-rays comprising a radiation source which generates X-rays and a lens system which directs the X-ray beam. The X-ray lens system is configured to focus X-rays to a focal point and vary the intensity of said focal point.

U.S. Pat. No. 7,068,754 discloses an X-ray apparatus including a ring anode to emit radiation, and a conical monochromator to monochromatize the emitted radiation. An outer diameter of the ring anode is greater than an outer diameter of a base of the monochromator.

SUMMARY OF THE INVENTION

It is hence one object of the invention to disclose an X-ray lens arrangement for forming a radiation pattern as a focal track. The lens arrangement is longitudinally arranged for Bragg X-ray diffraction of the X-ray.

It is a core purpose of the invention to provide the radiation pattern which is a three-dimensional curve.

It is a further core purpose of the invention to provide the pattern configured as at least one three-dimensional focal track of radiation. The lens arrangement has a main axis passing through intensity weighted centroids of the X-ray source and the pattern. The arrangement comprises at least one reflecting surface of the lens of continuously varying Rowland arcs. Each point belonging to the focal track is linked to an elemental point composing an emitting surface of the source by a corresponding Rowland arc.

Another object of this disclosure is to disclose the abovementioned invention wherein the source is a point source. The lens arrangement has a main axis passing through the point source and centroid of the pattern. Each point of the focal track is linked to the source by a corresponding Rowland arc.

A further object of this disclosure is to disclose the abovementioned invention wherein the reflecting surface is continuously defined by a Rowland arc of a constant radius.

A further object of this disclosure is to disclose the abovementioned invention wherein the reflecting surface is defined by continuously varying Rowland arcs of correspondingly varying radii.

A further object of this disclosure is to disclose the abovementioned invention wherein the focal track has a three-dimensional configuration.

A further object of this disclosure is to disclose the abovementioned invention wherein the focal track is in a plane whose normal is tilted relative to the main axis.

A further object of this disclosure is to disclose the abovementioned invention wherein a shape of at least one of the tracks is selected from the group consisting of an orthogon, a square, a triangle, a parallelogram, a rhomb, a polygon, an oval, and any combination thereof, where the shape can be defined longitudinally or transversely or in any angle relative to the main axis.

A further object of this disclosure is to disclose the abovementioned invention wherein the curved track is closed or open.

A further object of this disclosure is to disclose the abovementioned invention wherein the pattern comprises a plurality of focal tracks.

A further object of this disclosure is to disclose the abovementioned invention wherein the pattern comprises a plurality of focal tracks, where at least two of the said focal tracks are reflected from reflecting surfaces comprising the same crystallographic planes.

A further object of this disclosure is to disclose the abovementioned invention wherein the focal pattern comprises a plurality of three-dimensional focal tracks of non-symmetrical geometry.

A further object of this disclosure is to disclose the abovementioned invention wherein the focal pattern comprises a plurality of three-dimensional focal tracks of symmetrical geometry.

A further object of this disclosure is to disclose the abovementioned invention wherein the focal pattern comprises a plurality of coplanar focal tracks.

A further object of this disclosure is to disclose the abovementioned invention wherein the focal pattern comprises a plurality of noncoplanar focal tracks.

A further object of this disclosure is to disclose the abovementioned invention wherein the focal pattern comprises a plurality of focal tracks being in planes intersecting at lines passing through the main axis.

A further object of this disclosure is to disclose the abovementioned invention wherein the focal pattern comprises a plurality of focal tracks being in planes intersecting at lines not passing through the main axis.

A further object of this disclosure is to disclose the abovementioned invention wherein the focal pattern comprises a plurality of three-dimensional focal tracks longitudinally displaced therebetween.

A further object of this disclosure is to disclose the abovementioned invention wherein the focal pattern comprises a plurality of three-dimensional transversally shifted focal tracks.

A further object of this disclosure is to disclose the abovementioned invention wherein the focal pattern comprises a plurality of three-dimensional longitudinally shifted focal tracks.

A further object of this disclosure is to disclose the abovementioned invention wherein the plurality of curved tracks is concentric.

A further object of this disclosure is to disclose the abovementioned invention wherein the plurality of curved tracks is non-concentric.

A further object of this disclosure is to disclose an X-ray reflective lens arrangement for forming a radiation pattern in a focal region. The lens arrangement is longitudinally arranged for Bragg X-ray diffraction of the X-ray.

A further object of this disclosure is to disclose the abovementioned invention wherein the lens assembly comprises of an inverted image assembly.

It is a core purpose of the invention to provide the lens arrangement having a main axis passing through intensity weighted centroids of the X-Ray source and the pattern. The lens arrangement comprises at least one pair of oppositely oriented lenses placed along the main optical axis. Reflective surfaces of the first and second lens are continuously defined by Rowland arcs. The first lens is configured to focus a radiation from the X-ray source into an intermediate radiation pattern; the second lens is configured to further reflect the radiation of the intermediate pattern to form an output radiation pattern within the focal region.

A further object of this disclosure is to disclose the abovementioned invention wherein the X-ray source is point-like. Reflective surfaces of the first and second lens are defined by continuously varying Rowland arcs.

A further object of this disclosure is to disclose the abovementioned invention wherein the reflecting surfaces of oppositely oriented lenses are continuously defined by a Rowland arc of a constant radius.

A further object of this disclosure is to disclose the abovementioned invention wherein the reflecting surfaces of oppositely oriented lenses are defined by continuously varying Rowland arcs of correspondingly varying radii.

A further object of this disclosure is to disclose the abovementioned invention wherein the focal track formed by the double reflection arrangement has a three-dimensional configuration.

A further object of this disclosure is to disclose the abovementioned invention wherein the focal track formed by the double reflection arrangement is in a plane whose normal is tilted relative to the main axis.

A further object of this disclosure is to disclose the abovementioned invention wherein a shape of at least one of the track formed by the double reflection arrangement is selected from the group consisting of an orthogon, a square, a triangle, a parallelogram, a rhomb, a polygon, an oval, and any combination thereof, where the shape can be defined longitudinally or transversely or in any angle relative to the main axis.

A further object of this disclosure is to disclose the abovementioned invention wherein the curved track formed by the double reflection arrangement is closed or open.

A further object of this disclosure is to disclose the abovementioned invention wherein the pattern formed by the double reflection arrangement comprises a plurality of focal tracks.

A further object of this disclosure is to disclose the abovementioned invention wherein the pattern formed by the double reflection arrangement comprises a plurality of focal tracks, wherein the pattern comprises a plurality of focal tracks, where at least two of the said focal tracks are reflected from reflecting surfaces comprising the same crystallographic planes.

A further object of this disclosure is to disclose the abovementioned invention wherein the focal pattern formed by the double reflection arrangement comprises a plurality of three-dimensional focal tracks of non-symmetrical geometry.

A further object of this disclosure is to disclose the abovementioned invention wherein the focal pattern formed by the double reflection arrangement comprises a plurality of three-dimensional focal tracks of symmetrical geometry.

A further object of this disclosure is to disclose the abovementioned invention wherein the focal pattern formed by the double reflection arrangement comprises a plurality of coplanar focal tracks.

A further object of this disclosure is to disclose the abovementioned invention wherein the focal pattern formed by the double reflection arrangement comprises a plurality of noncoplanar focal tracks.

A further object of this disclosure is to disclose the abovementioned invention wherein the focal pattern formed by the double reflection arrangement comprises a plurality of focal tracks being in planes intersecting at lines passing through the main axis.

A further object of this disclosure is to disclose the abovementioned invention wherein the focal pattern formed by the double reflection arrangement comprises a plurality of focal tracks being in planes intersecting at lines not passing through the main axis.

A further object of this disclosure is to disclose the abovementioned invention wherein the focal pattern formed by the double reflection arrangement comprises a plurality of three-dimensional focal tracks are longitudinally displaced therebetween.

A further object of this disclosure is to disclose the abovementioned invention wherein the focal pattern formed by the double reflection arrangement comprises a plurality of three-dimensional transversally shifted focal tracks.

A further object of this disclosure is to disclose the abovementioned invention wherein the focal pattern formed by the double reflection arrangement comprises a plurality of three-dimensional longitudinally shifted focal tracks.

A further object of this disclosure is to disclose the abovementioned invention wherein the plurality of curved tracks formed by the double reflection arrangement is concentric.

A further object of this disclosure is to disclose the abovementioned invention wherein the plurality of curved tracks formed by the double reflection arrangement is nonconcentric.

A further object of this disclosure is to disclose the abovementioned invention wherein the lens assembly comprises an inverted image assembly.

A further object of this disclosure is to disclose a method of forming an X-ray radiation pattern in a focal region such that the radiation pattern is configured as a curved track.

A further object of this disclosure is to disclose a method of forming an X-ray radiation pattern in a focal region. The aforesaid method comprises the steps of: (a) providing an X-ray source; (b) providing a reflective lens arrangement longitudinally arranged for Bragg X-ray diffraction of the X-rays; and (c) forming the radiation pattern in the focal region.

It is a further core purpose of the invention to provide the pattern formed as at least one three-dimensional curved focal shape of radiation. The step of forming the radiation pattern is performed by the lens arrangement having a main axis passing through intensity weighted centroids of an X-Ray source and the focal track. The arrangement comprises at least one reflecting surface of the lens of continuously varying Rowland arcs; each point belonging to the point ensemble of the focal track is linked to an elemental point of a source emitting surface by a corresponding Rowland arc.

A further object of this disclosure is to disclose the abovementioned invention wherein the step of forming the radiation pattern is performed by the source being point-like. The lens arrangement has a main axis passing through the point source and centroid of the pattern. Each point of the focal track is linked to the source by a corresponding Rowland arc.

A further object of this disclosure is to disclose the abovementioned invention wherein the lens assembly comprises at least one lens arrangement nested within said assembly.

A further object of this disclosure is to disclose a method of forming a radiation pattern in a focal region. The aforesaid method comprises the steps of: (a) providing an X-ray source; (b) providing a reflective lens arrangement longitudinally arranged for Bragg X-ray diffraction of the X-rays; (c) forming the radiation pattern in the focal region.

It is a further core purpose of the invention to provide the step of forming the radiation pattern performed by the lens arrangement having a main axis passing through the intensity weighted centroids of the X-ray source and the pattern. The arrangement comprises at least one pair of oppositely oriented lenses which are placed along the main optical axis forming a double lens setup. Reflective surfaces of the first and second lenses are defined by continuously varying Rowland arcs connecting each elemental point of the source to a corresponding elemental point of the focal track. The first lens is configured to focus radiation from the X-ray source into an intermediate radiation pattern. The second lens is configured to further reflect the radiation of the intermediate pattern to the output radiation pattern within the focal region.

A further object of this disclosure is to disclose the abovementioned invention wherein the step forming of the radiation pattern comprises forming an inverted image.

A further object of this disclosure is to disclose the abovementioned invention wherein the step of forming the radiation pattern is performed by a point-like source. Reflective surfaces of the first and second lenses are defined by continuously varying Rowland arcs.

A further object of this disclosure is to disclose the abovementioned invention wherein a lens design comprises at least one ring holding Bragg reflector single crystals. Each ring contains Bragg reflectors cut and polished to the same crystallographic plane with more than one ring, having Bragg reflector single crystals cut and polished to the same crystallographic plane.

BRIEF DESCRIPTION OF THE DRAWINGS

In order to understand the invention and to see how it may be implemented in practice, a plurality of embodiments is now be described, by way of non-limiting example only, with reference to the accompanying drawings, in which.

DETAILED DESCRIPTION OF THE INVENTION

The following description is provided, alongside all chapters of the present invention, so as to enable any person skilled in the art to make use of the aforesaid invention, and sets forth the best modes contemplated by the inventor of carrying out this invention. Various modifications, however, are adapted to remain apparent to those skilled in the art, since the generic principles of the present invention have been defined specifically to provide an X-ray reflective lens arrangement for forming an intensity pattern in a focal region and methods of using the same.

The term "elemental" hereinafter refers to infinitely small portion of a physical entity.

The term "focal track" hereinafter refers to an ordered ensemble of elemental focal points created by a reflecting surface of an X-ray lens.

The term "intensity weighted centroid of the X-ray source" hereinafter refers to a point defined by a vector $\vec{r}_{sc}$ $$\vec{r}_{sc} = \frac{\int_{\substack{complete \\ source\ shape}} I_{source}(x, y, z)\vec{r}dV}{\int_{\substack{complete \\ source\ shape}} I_{source}(x, y, z)dV}$$

$$= \frac{\int_{\substack{complete \\ source\ shape}} I_{source}(x, y, z)\vec{r}dV}{I_{source\_total}}.$$

The term "intensity weighted centroid of the focal pattern" hereinafter refers to a point defined by a vector $\vec{r}_{fc}$ $$\vec{r}_{fc} = \frac{\int_{\substack{complete \\ focal\ shape}} I_{focus}(x, y, z)\vec{r}dV}{\int_{\substack{complete \\ focal\ shape}} I_{focus}(x, y, z)dV}$$

$$= \frac{\int_{\substack{complete \\ focal\ shape}} I_{focus}(x, y, z)\vec{r}dV}{I_{focus\_total}}.$$

$I_{focus}(x,y,z)$ is a spatial distribution of radiation intensity in the focal region, and $I_{source}(x,y,z)$ is the spatial distribution of source intensity at the source space. It should be appreciated that the radiation pattern has a three-dimensional shape.

Referring to the medical use of the X-ray system for tumor treatment, the known therapeutic devices comprising focusing elements are characterized by concentration of X-ray radiation into a sharp focal spot. It should be emphasized that uniform X-ray exposure of a target volume is a desirable condition of successful therapy or surgery because the optimal effect is achieved when all target tissue is exposed to a uniform dose. Thus, there is a long-felt and unmet need to provide a therapeutic device for X-ray treatment of tumors adapted for forming substantially uniform X-ray intensity within the target volume.

Figure 1:
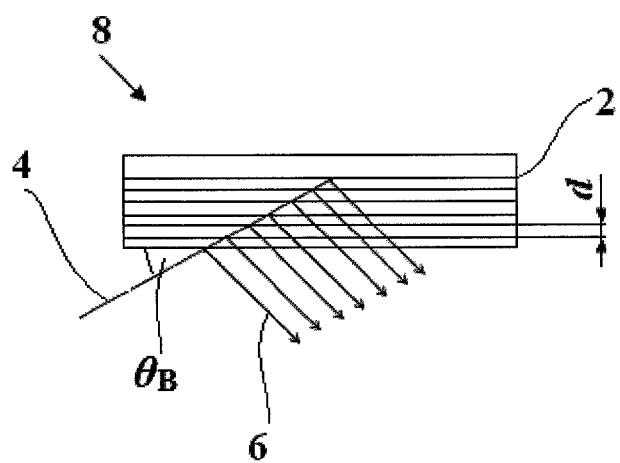
FIG. 1 is a schematic partial longitudinal cross sectional view of a crystal element with schematic reflection planes of an X-ray lens.

Reference is now made to FIG. 1, illustrating a simple Bragg reflector utilizing the principles of Bragg reflection. X-ray radiation 4 of wavelength λ is incident on a crystal having lattice planes 2 of plane spacing d. Narrow band or generally monochromatic radiation 6 is then reflected according to Bragg's Law. Bragg structures only reflect radiation when Bragg's equation is satisfied:

$$n\lambda = 2d \sin \theta_B, \quad (1)$$

where n is the reflection order, λ is the incident radiation wavelength, d is the lattice plane spacing, and $\theta_B$ is the Bragg angle.

Figure 2:
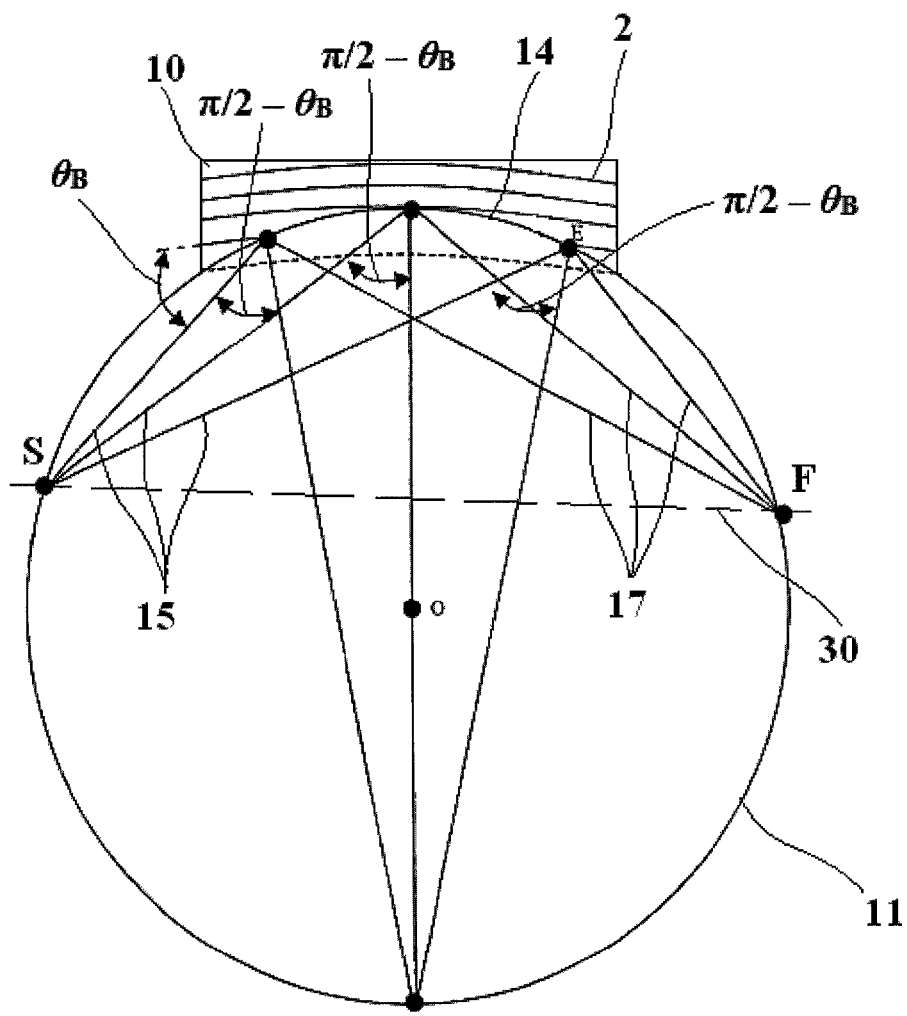
FIG. 2 is a two-dimensional diagram of the Johansson scheme.

Reference is now made to FIG. 2, presenting a two-dimensional longitudinal cut of the Johansson scheme. A Johansson bent and machined crystal 10 is used to reflect and focus X-rays. The Johansson bent and machined crystal 10 reflects X-rays according to Bragg's law. The Johansson crystal 10 is made by bending and grinding a crystal into a barrel shaped surface with a longitudinal bending radius 2R, and then the reflection surface 14 is machined to a cylindrical surface with longitudinal radius R. In a special symmetrical case, the angles of incidence of rays 15 generated by the X-ray source S and angles of reflection of rays 17 converging into the point F, are equal.

The transversal curvature radius of the machined surface at a midpoint between the source and the focal point $r_s$ is given by $$r_s = L \tan \theta_B, \quad (2)$$

L is half of the distance from the source to the focal point.

The Rowland radius R is given by the following expression $$R = \frac{r_s}{2\sin^2 \theta_B}. \quad (3)$$

Figure 3:
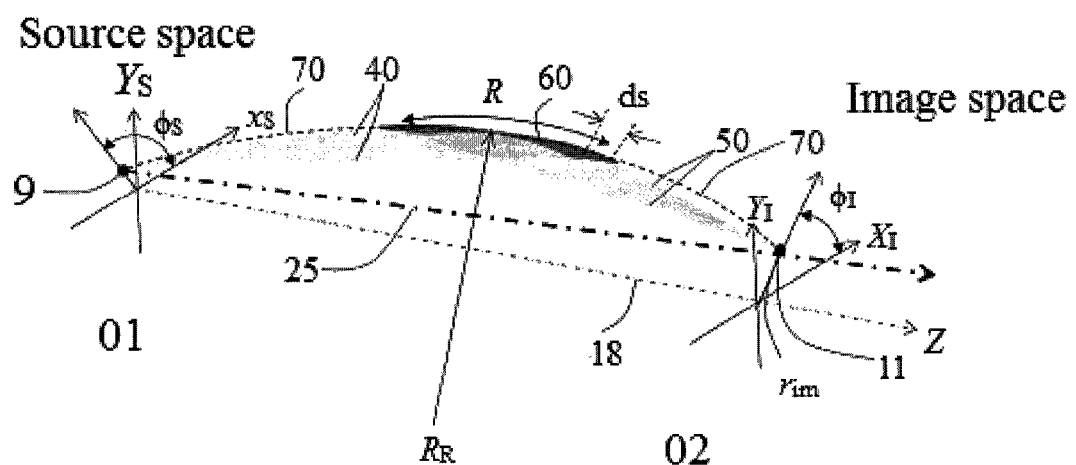
FIG. 3 is a schematic presentation of the elemental reflective lens.

Reference is now made to FIG. 3, elucidating a subject matter of the current invention. An elemental point 11 is a part of the image of an elemental X-ray source point 9 in source space $X_S Y_S$ formed by an elemental portion 60 of reflective lens which lies in a Rowland arc 70 subtended by a chord 25. Lines 40 and 50 refer to rays emitted by the X-ray source elemental point 9 and reflected from the lens portion 60, respectively. An axis 18 is a main axis of the entire lens. The chord 25 is the optical axis of the narrow reflective lens portion 60. The aforesaid point 11 is at location $r_{im}$ on the $X_I Y_I$ plane of the image space.

The elemental point source 9 makes an angle $\phi_S$ relative to the $X_S$ axis in source space.

The elemental point 11 makes an angle $\phi_I$ relative to the $X_I$ axis in image space, wherein $\phi_S$ and $\phi_I$ are generally not the same, thus in general the image point 11 can be rotated relative to the source point 9.

Figure 4:
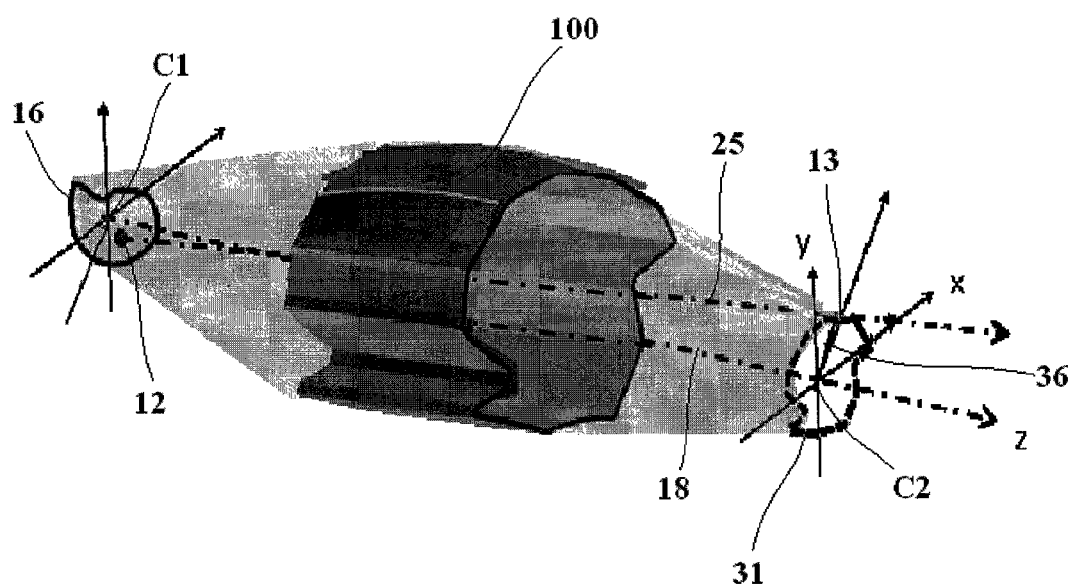
FIG. 4 is a general schematic view of the lens arrangement.

Reference is now made to FIG. 4, presenting a lens arrangement 100 continuously defined by an ensemble of elemental arcs 60 being rotated around the main axis 18. The lens arrangement 100 focuses radiation emitted by the X-ray source 12 into a curved radiation pattern 31. It should be emphasized that the curved pattern of radiation pattern 31 is an ensemble of elemental points 11 (not shown) created by the plurality of elemental arcs 60 integrally forming the reflective surface 100.

The main axis 18 is defined by two points which are: (1) the intensity weighted centroid C1 of the X-ray source, and (2) a centroid C2 of the linear radiation pattern 30. The centroids are intensity weighted average points of the source and the radiation patter 31.

Figure 5:
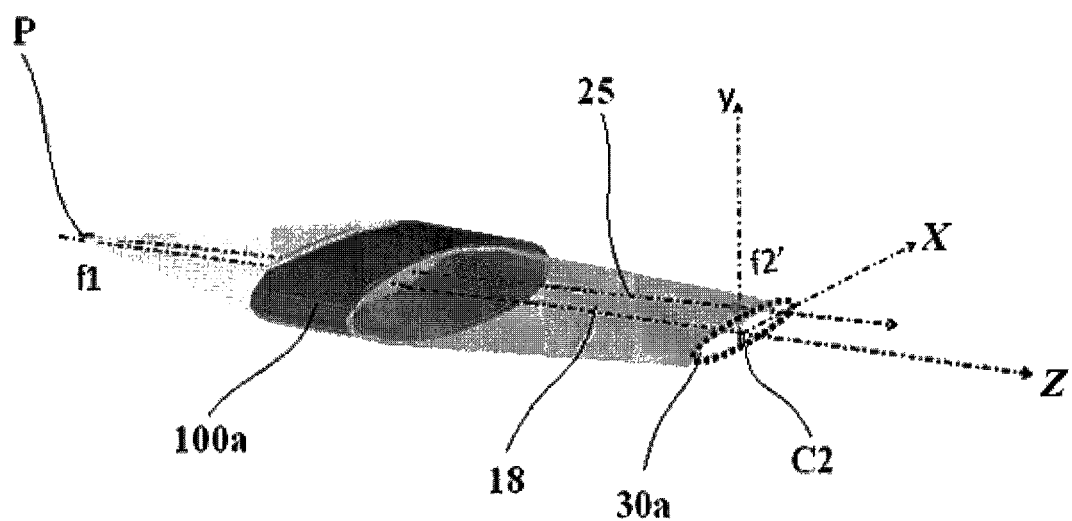
FIGS. 5 and 6 are schematic views of the exemplary embodiments of the lens arrangement.
Figure 6:
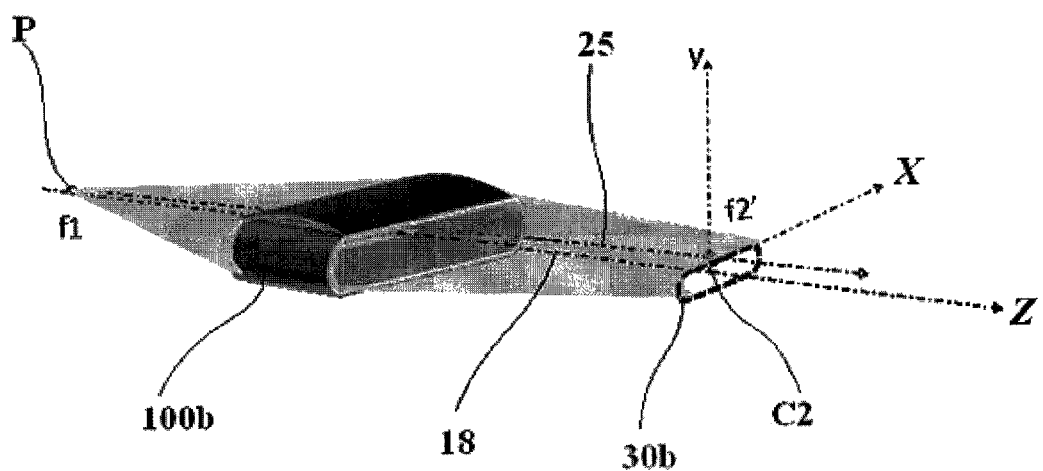

Reference is now made to FIGS. 5 and 6, presenting exemplary embodiments of the current invention. Specifically, a lens arrangement 100a is configured to provide an elliptic radiation pattern 30a while a lens arrangement 100b focuses radiation from the X-ray source into an orthogon 30b with rounded angles. The designation P refers to a point source.

Figure 7:
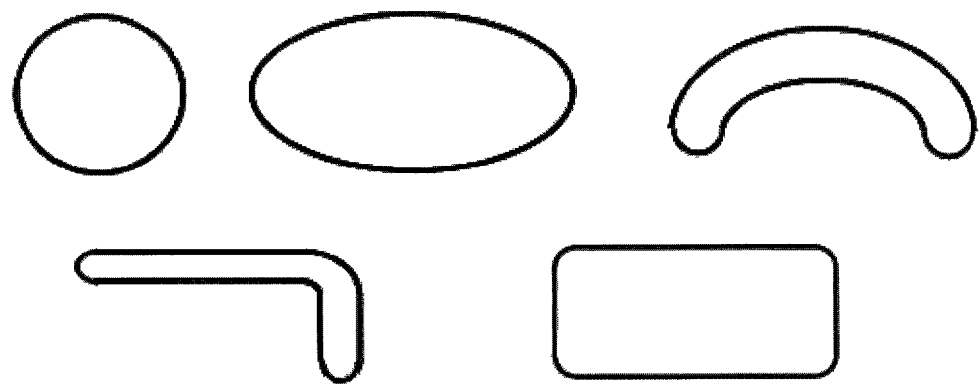
FIGS. 7 to 9 are schematic views of the exemplary radiation patterns.
Figure 8:
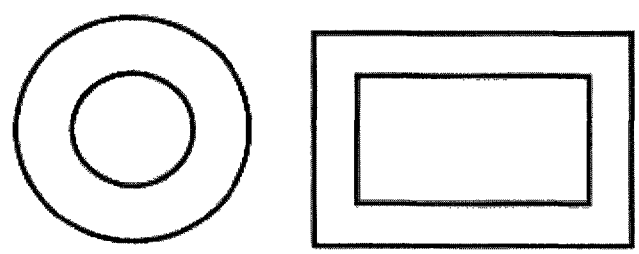
Figure 9:
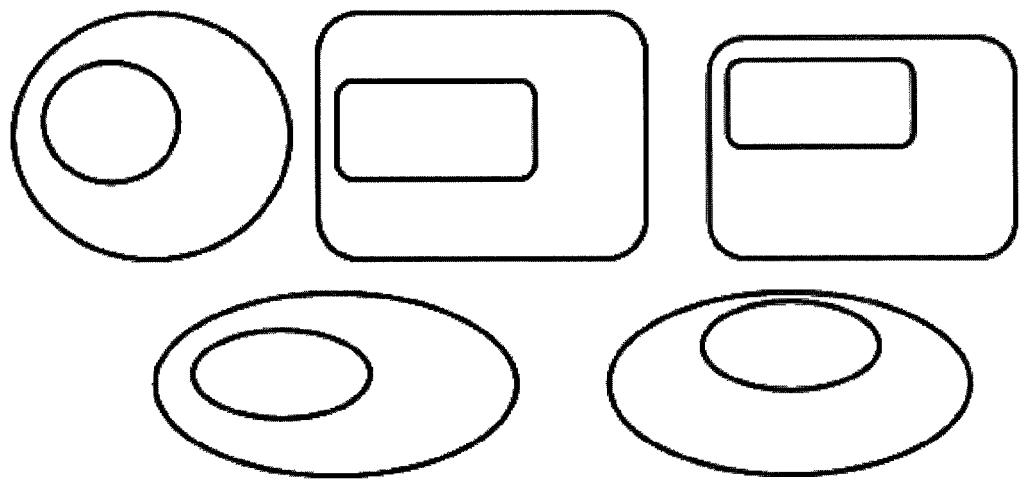

Reference is now made to FIGS. 7 to 9, presenting exemplary radiation patterns focused by optional embodiments of the current invention. Simple closed curves radiation patterns are shown in FIG. 7. The radiation patterns comprising two curved radiation tracks (one inside another) are depicted in FIG. 8 (concentric radiation patterns) and FIG. 9 (non-concentric radiation patterns).

Figure 10:
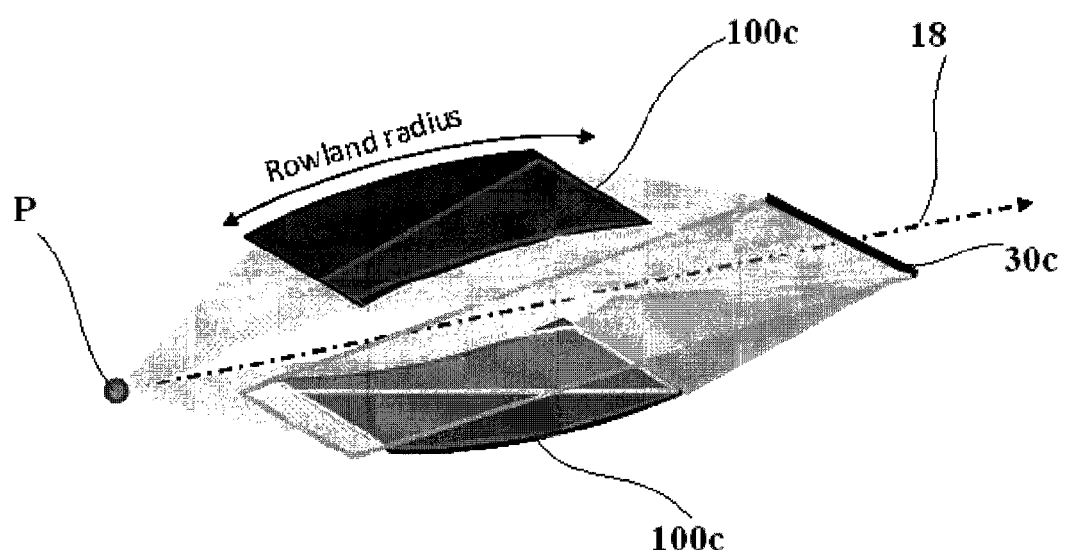
FIG. 10 is a schematic view of an exemplary embodiment of an open lens arrangement.

Reference is now made to FIG. 10, presenting an alternative embodiment of the current invention. A lens arrangement 100c is portioned into two parts, which are configured to provide the X-ray radiation into same curved radiation pattern 30c.

Figure 11:
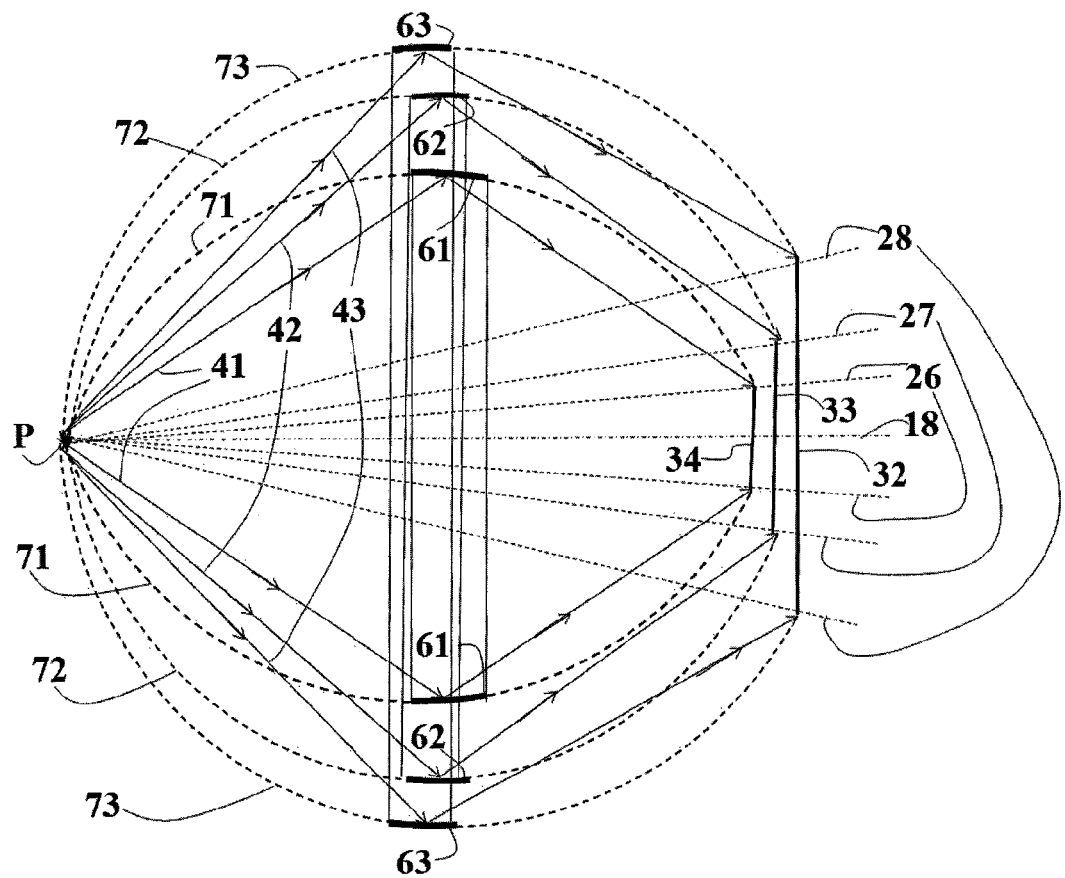
FIG. 11 is a schematic view of the lens arrangement comprising the plurality of reflective surfaces.

Reference is now made to FIG. 11, presenting a cross-sectional schematic view of a lens arrangement of the current invention which comprises a plurality of reflective surfaces (for example, three surfaces 61, 62 and 63). The aforesaid tracks are formed by revolution of Rowland arcs 71, 72 and 73 around the main axis 18, and its elemental image are defined as intersection chords 26, 27 and 28 with the corresponding arcs 71, 72 and 73, respectively. The reflective surface 61, 62 and 63 reflect the radiation emitted by the point source P to ring-like radiation patterns 32, 33 and 34, respectively. The chords 26, 27 and 28 extend from the point source P, and are tilted in this example to the main axis 18 of the lens arrangement. Thus, at output of the lens arrangement, a resulting radiation pattern comprising a plurality of the ring-like radiation patterns 32, 33 and 34 is provided. The aforesaid patterns are distributed over the main axis 18.

Figure 12:
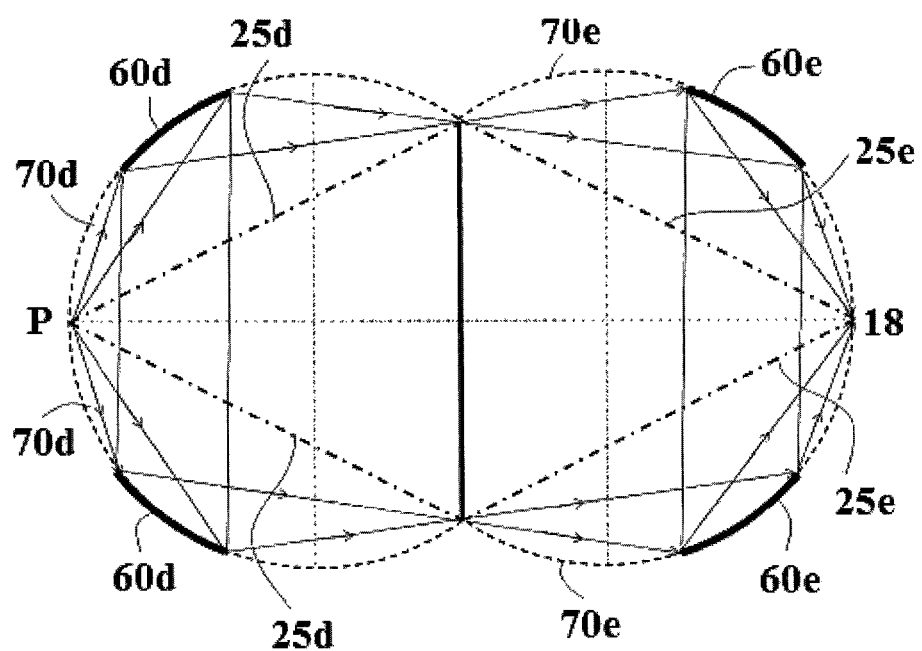
FIG. 12 is a schematic view of the lens arrangement with the double lens setup.

Reference is now made to FIG. 12, presenting a cross-sectional schematic view of a double reflection lens arrangement. The lens arrangement comprises a pair of oppositely directed reflective surfaces 60d and 60e residing on the Rowland arcs 70d and 70e which are subtended by chords 25d and 25e, respectively. Specifically, the reflective surface 60d provides a ring-like radiation pattern 31a. Then, the reflective surface 60e further reflects the radiation of the pattern 31a into a point pattern 30d. A significant advantage of the depicted double reflection lens arrangement is in providing a wide-angle convergent beam essentially to a surface region of a patient's body without extensive damage to surrounding tissues and the use of low order high reflective crystallographic planes for more than one reflective ring. The wide angle of the beam convergence results in very quick drop in radiation in a space behind the focus point 30d. Thus, the proposed lens arrangement can be effectively used for X-ray therapy of surface tumors. It also enables having a relatively large lens for higher solid angle of radiation collection.

Figure 13:
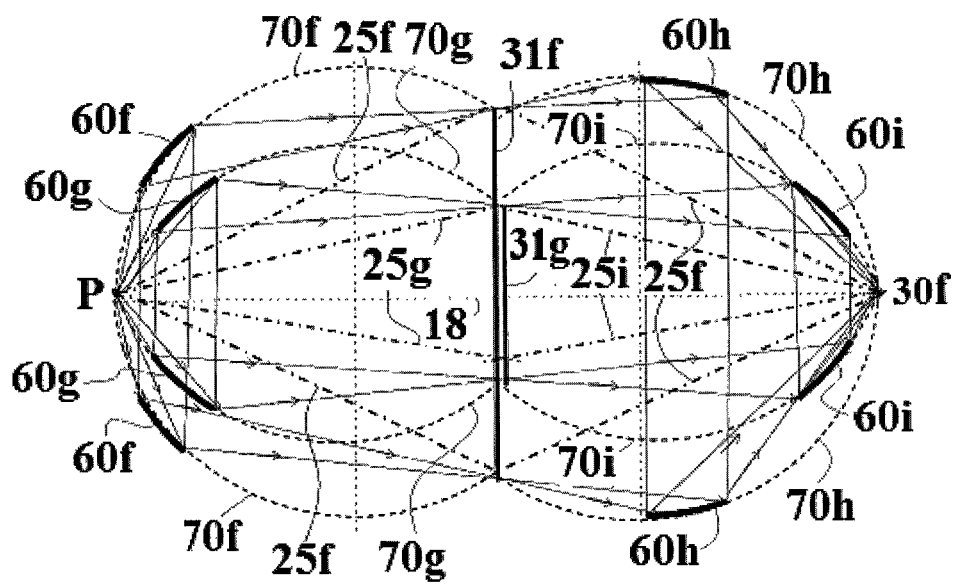
FIGS. 13 and 14 are schematic views of the lens arrangement with the double lens wide convergence angle comprising the plurality of reflective surfaces.

Reference is now made to FIG. 13, presenting a cross-sectional schematic view of a lens arrangement comprising two pluralities of reflective surfaces (for example, two surfaces in each plurality). Radiation from the point source P is focused by reflecting surfaces 60g and 60f into ring-like radiation patterns 31f and 31g, respectively. Then, the aforesaid radiation from patterns 31f and 31g are further reflected by surfaces 60h and 60i into a point radiation pattern 30f. The Rowland arcs 70f, 70g, 70h and 70i are subtended by chords 25f, 25g, 25h and 25i, respectively.

Figure 14:
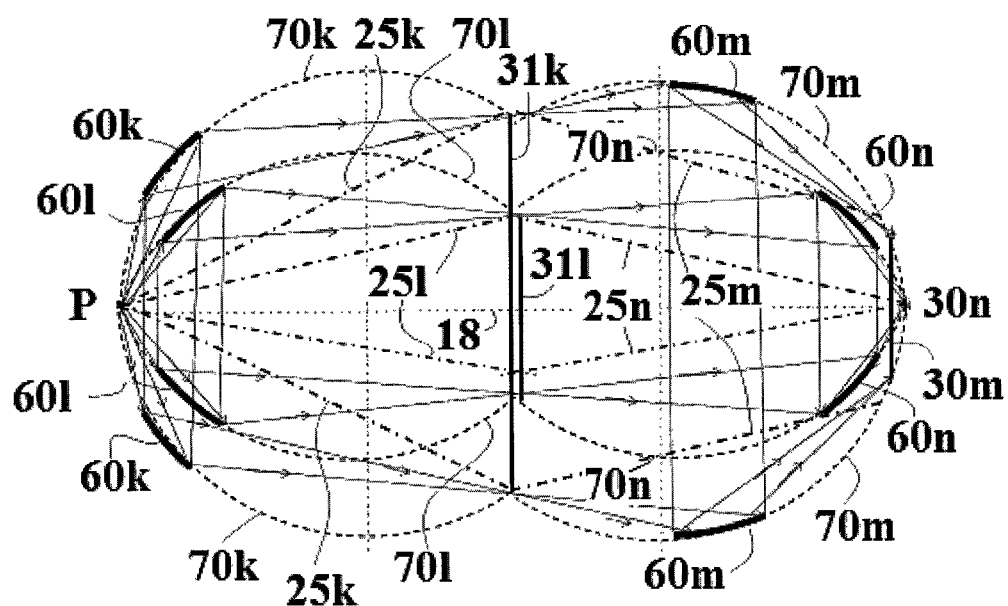

Reference is now made to FIG. 14, presenting a cross-sectional schematic view of an alternative embodiment of the current invention. The lens arrangement provides an output radiation pattern comprising a point focal spot 30n and at least one ring-like pattern 30m. Radiation from the point source P is focused by reflecting surfaces 60k and 60l into ring-like radiation patterns 31k and 31l, respectively. Then, the aforesaid radiation from patterns 31k and 31l are further reflected by surfaces 60m and 60n into a ring-like pattern 30m and a point radiation pattern 30n, respectively. The Rowland arcs 70k, 70l, 70m and 70n are subtended by chords 25k, 25l, 25m and 25n, respectively.

Figure 15:
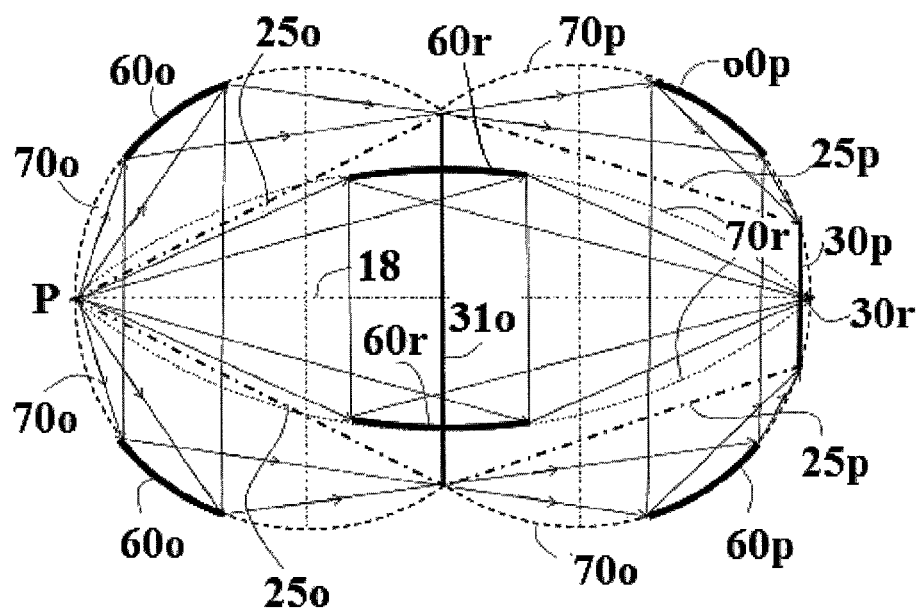
FIG. 15 is a schematic view of an exemplary combined lens arrangement comprising the single lens nested within a double lens arrangement.

Reference is now made to FIG. 15, presenting an exemplary combined lens arrangement comprising at least one single-reflection lens and at least one double reflection lens assembly. Specifically, the combined arrangement comprises of a single lens 60r and a double reflection lens arrangement 60o-60p. Each component (single and double lens arrangements) can be replaced with a plurality of similar elements. In addition, each element can be configured for focusing point or non-point source into any focal point or focal track.

One core purpose of the proposed invention is to describe a lens array design for providing higher efficiency in transmitting the radiation from the x-ray tube to the focul track. For example, the known technical solutions comprise a multiplicity of rings containing Bragg reflector single crystals. However, the present invention, concentrates the radiation within the targeted volume and different rings required crystals cut in different crystallographic planes. However, different crystallographic planes do not have the same reflectivities. Therefore some rings' crystals have higher efficiency than others. The present invention overcoms this limitation and allows the higher efficiency crystal orientations to be used in multiple rings. The proposed technical solution significantly improves the overall efficiency of a lens array and provides more efficient lens array designs which can reduce exposure times or reduce lens complexity for equivalent exposure times.

Figure 16:
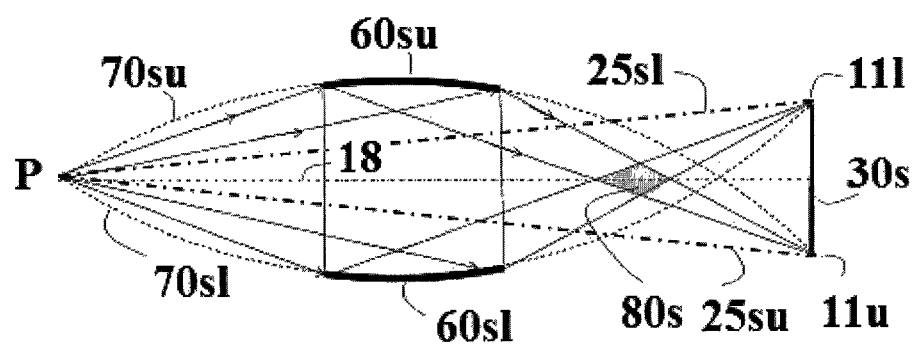
FIG. 16 is a schematic view of an exemplary lens comprising an inverted image assembly and FIG. 17 is a schematic view of an exemplary double lens wide convergence angle comprising an inverted image assembly.

Reference is now made to FIG. 16, presenting an exemplary lens comprising an inverted image assembly. The lens arrangement is designed so that each of the elemental image points 11l and 11u belongs to opposite elemental lenses. The aforesaid points called inverted points are located in the same plane defined by their Rowland arcs. For example, the inverted points 11l and 11u are opposite to each other on the ring focal track 30s relative to the elemental surface 60su and 60sl which produced them.

In the drawing, the lower and upper drawn cuts of the elements in the drawings are labeled separately. Lens upper surface is labeled 60su and the lower part in the drawing is labeled 60sl. The same applies to the Rowland arcs, 70su for upper drawing and 70sl for the lower drawing and also for the cords suspending the Rowland arcs 25su and 25sl and the elemental image points 11u and 11l connected to the X-rays shown as being a part of the ring 30w.

It should be emphasized that the two points 11u and 11l lay oppositely with respect to the symmetry line 18 that passes between them in their mutual plane containing the two inverted points.

Figure 17:
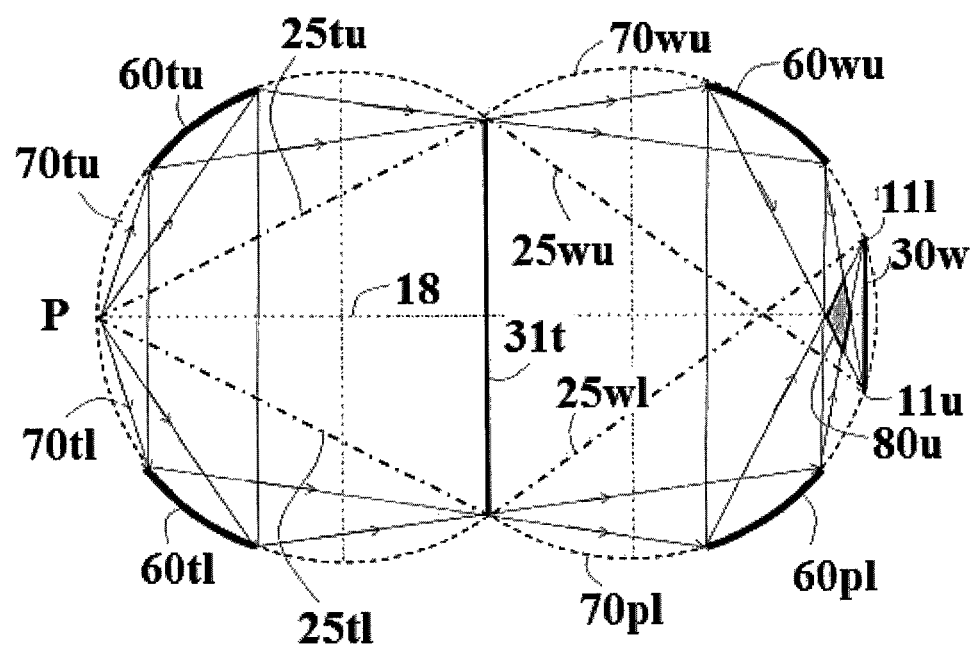

Reference is now made to FIG. 17 presenting double lens wide convergence angle comprising an inverted image assembly. An approach similar to FIG. 16 is a double lens wide convergence angle setup, comprising an inverted image assembly applied also to double reflection assembly. The second reflector 60wu and 60pl flips the inverted points 11u and 11l on their mutual plane. This type of assembly hereinafter refers will be referred to as "inverted image assembly"

The advantages of the present design solution are the following. An inverted image assembly causes the intersection of rays from the inverted sides of each plane containing the inverted points. The area of intersection can be seen as 80s in a single reflection assembly of FIGS. 16 and 80u in the double reflection assembly of FIG. 17. Summing up the X-ray radiation from the entire surface of the lens forms a secondary concentration around the symmetry line that results in a somewhat higher dose along the symmetry line.

Concerning the ordinary non-inverted design solutions, the overlapping areas where secondary concentration of X-ray radiation occurs, are located behind the target volume of treatment. This is relatively distant from the location where the radiation has passed the volume of treatment. Thus the radiation damage effect is much weaker due to attenuation of the beam and divergence angle of the X-ray beam.

The strength of the effect depends on the convergence angle and the width of the reflecting surface. These parameters are controllable by means of changing design parameters. This approach is especially effective in the double reflection assembly where the overlapping area is close to the treated volume. This can serve as part of the treatment plan improving the capability and control of the treated volume. The embodiments depicted in FIGS. 16 and 17 are more effective for treatment of a shallow tumor, since the intersection area will occur before the X-rays hit the body, while the non inverted embodiments are more effective for deeper tumor treatments since the intersection area is a minor phenomenon or located outside of the patient's body.

An additional benefit of the current invention is in the use of single crystals exhibiting some degree of mosaicity. The focal tracks thus created by the present invention are characterized by three-dimensional broadening which serves the purpose of allowing for homogeneity of the created radiation pattern within the target volume.

The present invention is specifically advantageous in assembling multiple reflecting surfaces of elements having the same crystallographic plane index for different surfaces. In the case of double reflection arrangement, the dependency of the setup on Bragg angle is further avoided, and thus the limitations caused by higher order low reflectivity Miller index are overcome. Thus, the present invention provides multiple low order and high reflectivity surfaces.

Special benefits can be made in cases where the body has to be irradiated from the front, e.g. after breast mastectomy. The existing technology provides irradiation of the entire depth of the body over relatively large area. The current invention provides a high convergence angle. Thus, utilizing the high convergence angle yields a large attenuation after the target volume, spearing healthy tissues.

The invention claimed is:

1. An X-ray reflective lens arrangement for forming a radiation pattern in a focal region; said lens arrangement is longitudinally arranged for Bragg X-ray diffraction of the X-ray; wherein said lens arrangement has a main axis passing through intensity weighted centroids of the X-Ray source and the pattern; said lens arrangement comprises at least one pair of oppositely oriented lenses placed along said main optical axis; reflective surfaces of said first and second lens are continuously defined by Rowland arcs; said first lens is configured to focus a radiation from the X-ray source into an intermediate radiation pattern; said second lens is configured to further reflect said radiation of said intermediate pattern to form an output radiation pattern within said focal region.

2. The lens arrangement according to claim 1, wherein said X-ray source is point-like; reflective surfaces of the said and second lens are defined by continuously varying Rowland arcs.

3. The lens arrangement according to claim 1, wherein at least one of the following is true:
   a. said reflecting surface is continuously defined by a Rowland arc of a constant radius;
   b. said reflecting surface is defined by continuously varying Rowland arcs of correspondingly varying radii; and
   c. said focal track has a three-dimensional configuration.

4. The lens arrangement according to claim 1, wherein at least one of the following is true:
   a. said focal track is in a plane whose normal is tilted relative to the main axis;
   b. a shape of at least one of the track is selected from the group consisting of an orthogon, a square, a triangle, a parallelogram, a rhomb, a polygon, an oval, and any combination thereof, where the shape can be defined transversely to the main axis;
   c. a shape of at least one of the track is selected from the group consisting of an orthogon, a square, a triangle, a parallelogram, a rhomb, a polygon, an oval, and any combination thereof, where the shape can be defined longitudinally relative to the main axis;
   d. a shape of at least one of the track is selected from the group consisting of an orthogon, a square, a triangle, a parallelogram, a rhomb, a polygon, an oval, and any combination thereof, where the shape can be defined in an angle relative to the main axis.

5. The lens arrangement according to claim 1, wherein at least one of the following is true:
   a. said curved track is closed;
   b. said curved track is open; and
   c. said pattern comprises a plurality of focal tracks.

6. The lens arrangement according to claim 1, wherein at least one of the following is true:
   a. said pattern comprises a plurality of focal tracks, wherein said pattern comprises a plurality of focal tracks, where at least two of the said focal tracks are reflected from reflecting surfaces processed at the same crystallographic planes;
   b. said focal pattern comprises a plurality of three-dimensional focal tracks of non-symmetrical geometry; and
   c. said focal pattern comprises a plurality of three-dimensional focal tracks of symmetrical geometry.

7. The lens arrangement according to claim 1, wherein at least one of the following is true:
   a. said focal pattern comprises a plurality of coplanar focal tracks;
   b. said focal pattern comprises a plurality of noncoplanar focal tracks; and
   c. said focal track is in a plane whose normal is tilted relative to the main axis.

8. The lens arrangement according to claim 1, wherein said lens is of an inverted image type.

* * * * *